(12) United States Patent
Nappa et al.

(10) Patent No.: US 8,354,039 B2
(45) Date of Patent: Jan. 15, 2013

(54) PROCESS FOR THE MANUFACTURE FLUOROCARBONS

(75) Inventors: Mario Joseph Nappa, Newark, DE (US); Velliyur Nott Mallikarjuna Rao, Wilmington, DE (US); Allen Capron Sievert, Elkton, MD (US); Jeffrey P. Knapp, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/153,580

(22) Filed: Jun. 6, 2011

(65) Prior Publication Data

US 2011/0237847 A1    Sep. 29, 2011

Related U.S. Application Data

(62) Division of application No. 12/440,040, filed as application No. PCT/US2007/019313 on Sep. 5, 2007, now Pat. No. 7,981,311.

(60) Provisional application No. 60/842,550, filed on Sep. 5, 2006.

(51) Int. Cl.
  *C09K 5/04* (2006.01)
  *C07C 17/383* (2006.01)
(52) U.S. Cl. .......... 252/67; 510/177; 510/408; 510/412; 570/178
(58) Field of Classification Search .................... 252/67; 510/177, 408, 412; 570/178
See application file for complete search history.

(56) References Cited

U.S. PATENT DOCUMENTS

| | | | | |
|---|---|---|---|---|
| 5,264,639 A * | 11/1993 | Morikawa et al. | ............ | 570/168 |
| 5,563,304 A * | 10/1996 | Rao et al. | ........................ | 570/166 |
| 5,626,790 A * | 5/1997 | Minor | .............................. | 252/67 |
| 5,670,079 A * | 9/1997 | Lunger et al. | ........................ | 252/67 |
| 6,184,426 B1 * | 2/2001 | Belen'Kill et al. | ............ | 570/172 |
| 6,352,648 B1 * | 3/2002 | Guglielmi et al. | ................ | 252/8 |
| 6,388,147 B1 * | 5/2002 | Rao et al. | ........................ | 570/166 |
| 6,472,574 B2 * | 10/2002 | Rao et al. | ........................ | 570/164 |
| 7,135,601 B2 * | 11/2006 | Mukhopadhyay et al. | ... | 570/226 |
| 7,700,004 B2 * | 4/2010 | Nappa et al. | .................... | 252/364 |
| 7,959,828 B2 * | 6/2011 | Nappa et al. | .................... | 252/364 |
| 7,981,312 B2 * | 7/2011 | Nappa et al. | .................... | 252/67 |
| 8,133,406 B2 * | 3/2012 | Nappa et al. | .................... | 252/67 |
| 2002/0128526 A1 * | 9/2002 | Rao et al. | ........................ | 570/166 |
| 2003/0122103 A1 * | 7/2003 | Sievert et al. | ................... | 252/67 |
| 2005/0080302 A1 * | 4/2005 | Baker et al. | .................... | 570/172 |
| 2006/0094911 A1 * | 5/2006 | Rao et al. | ........................ | 570/155 |
| 2006/0106263 A1 * | 5/2006 | Miller et al. | .................. | 570/155 |
| 2006/0217577 A1 * | 9/2006 | Mukhopadhyay et al. | ... | 570/156 |
| 2008/0051612 A1 * | 2/2008 | Knapp et al. | .................... | 570/178 |
| 2009/0005618 A1 * | 1/2009 | Rao et al. | ...................... | 570/178 |
| 2009/0124836 A1 * | 5/2009 | Rao et al. | ...................... | 570/134 |
| 2009/0137853 A1 * | 5/2009 | Rao et al. | ...................... | 570/169 |
| 2009/0267022 A1 * | 10/2009 | Nappa et al. | ............. | 252/182.12 |
| 2009/0306438 A1 * | 12/2009 | Sievert et al. | ................. | 570/157 |
| 2010/0025620 A1 * | 2/2010 | Nappa et al. | .................... | 252/67 |
| 2010/0051853 A1 * | 3/2010 | Rao et al. | ........................ | 252/67 |
| 2010/0076231 A1 * | 3/2010 | Nappa et al. | .................... | 570/156 |
| 2010/0210882 A1 * | 8/2010 | Sharratt et al. | ................ | 570/142 |
| 2010/0294979 A1 * | 11/2010 | Sievert | ............................ | 252/67 |
| 2010/0320412 A1 * | 12/2010 | Nappa et al. | .................... | 252/67 |
| 2011/0245350 A1 * | 10/2011 | Nappa et al. | .................. | 514/744 |

FOREIGN PATENT DOCUMENTS

| | | |
|---|---|---|
| JP | 06279328 | 10/1994 |
| WO | 9008754 A2 | 8/1990 |
| WO | WO 9008754 A * | 8/1990 |
| WO | WO 9101287 A1 * | 2/1991 |
| WO | WO 2008054778 A2 * | 5/2008 |

OTHER PUBLICATIONS

CAS Reg. No. 422-02-6, Nov. 16, 1984.*
Concise Science Dictionary, Oxford University Press, 1984, pp. 58, 59.*
T. Tanuma et al., "Ab initio 19-F NMR chemical shifts calculations for halogenated ethanes and propanes", Journal of Fluorine Chemistry, 99 (1990), 157-160.*
Henne, Fluorinated Derivatives of Propane, Journal of the American Chemical Society, 1937, vol. 59:2434-2436.
W. Schotte, Collection of Phase Equillbrium Data for Separation Technology, Ind. Eng. Chem. Process Des. Dev., 1980, vol. 19:432-439.

* cited by examiner

*Primary Examiner* — Douglas Mc Ginty

(57) ABSTRACT

Halocarbons of the structure $CF_3CF_2CH_2X$, wherein X is either F or Cl or mixtures thereof prepared by: contacting at least one 2-fluorochloropropane with hydrogen fluoride in a first fluorination step in the gas phase or liquid phase under substantially anhydrous conditions, in the absence of added catalyst to partially fluorinate said 2-fluorochloropropane; contacting said partially fluorinated 2-fluorochloropropane with at least the stoichiometric molar equivalent of hydrogen fluoride under substantially anhydrous conditions, in the presence of at least one fluorination catalyst in a second fluorination step; removing said reaction products from contact with said catalyst, and isolating a substantial yield of at least 1,1,1,2,2,3-hexafluoropropane or 1,1,1,2,2, penta-3-chloropropane, or mixtures thereof, respectively.

10 Claims, 2 Drawing Sheets

PROCESS FOR THE MANUFACTURE FLUOROCARBONS

CROSS REFERENCE(S) TO RELATED APPLICATION(S)

This application is a divisional of pending application Ser. No. 12/440,040, filed Mar. 5, 2009 as a National phase entry of PCT application PCT/US07/19313, filed Sep. 5, 2007, which claims the benefit of priority of U.S. Provisional Application 60/842,550, filed Sep. 5, 2006.

BACKGROUND INFORMATION

1. Field of the Disclosure

This disclosure relates in general to the preparation of halocarbons 3-chloro-1,1,1,2,2-pentafluoropropane (HCFC-235cb) and 1,1,1,2,2,3-hexafluoropropane (HFC-236cb), and azeotropic and near-azeotropic compositions comprising the fluorocarbons and hydrogen fluoride.

2. Description of the Related Art

The refrigeration industry has been working for the past few decades to find replacement refrigerants for the ozone depleting chlorofluorocarbons (CFCs) and hydrochlorofluorocarbons (HCFCs) being phased out as a result of the Montreal Protocol. The solution for most refrigerant producers has been the commercialization of hydrofluorocarbon (HFC) refrigerants. HFCs, however, are now being regulated due to concerns related to global warming.

There is always a need for new and better processes for the preparation of halocarbons that may be useful as refrigerants or in other applications such as foam expansion agents, aerosol propellants, fire suppression or extinguishing agents, solvents, and sterilants to name a few.

DESCRIPTION

Described is a composition comprising a halocarbon of the structure $CF_3CF_2CH_2X$, wherein X is either F or Cl or mixtures thereof prepared by:

contacting at least one 2-fluorochloropropane with hydrogen fluoride in a first fluorination step in the gas phase or liquid phase under substantially anhydrous conditions, in the absence of added catalyst to partially fluorinate said 2-fluorochloropropane;

contacting said partially fluorinated 2-fluorochloropropane with at least the stoichiometric molar equivalent of hydrogen fluoride under substantially anhydrous conditions, in the presence of at least one fluorination catalyst in a second fluorination step;

removing said reaction products from contact with said catalyst and isolating a substantial yield of at least 1,1,1,2,2,3-hexafluoropropane or 1,1,1,2,2, penta-3-chloropropane or mixtures thereof, respectively.

The process may further include the step after separating $CF_3CF_2CH_2X$ compounds and hydrogen fluoride (HF) from other components in the reaction product mixture (after the reaction products are removed from the catalyst by subjecting said reaction product mixture to a distillation step forming a column distillate composition comprising an azeotropic or near-azeotropic composition of said $CF_3CF_2CH_2X$ and hydrogen fluoride (HF) essentially free of chlorofluorocarbons.

Also described is a process for the preparation of halocarbons of the formula $CF_3CF_2CH_2X$, wherein X is either F or Cl or mixtures thereof, comprising contacting at least one 2-fluorochloropropane with hydrogen fluoride in a first fluorination step, in one embodiment, in the gas phase or in another embodiment, in the liquid phase under in another embodiment, substantially anhydrous conditions in the absence of added catalyst to partially fluorinate the 2-fluorochloropropane, followed by contacting the partially fluorinated 2-fluorochloropropane with at least the stoichiometric molar equivalent of hydrogen fluoride under substantially anhydrous conditions in a second fluorination step, in the presence of a fluorination catalyst, and removing the reaction products from the catalyst and separating said $CF_3CF_2CH_2X$ from other fluorochlorocarbons by forming a mixture of said $CF_3CF_2CH_2X$, other fluorochlorocarbons and hydrogen fluoride and subjecting said mixture to a distillation step forming a column distillate composition comprising an azeotropic or near-azeotropic composition of said $CF_3CF_2CH_2X$ and hydrogen fluoride essentially free of chlorofluorocarbons.

Further described are azeotropic or near-azeotropic compositions 1,1,1,2,2,3-hexafluoropropane and hydrogen fluoride and 1,1,1,2,2-pentafluoro-3-chloropropane and hydrogen fluoride.

Further described is a process for the separation of 1,1,1,2,2,3-hexafluoropropane from a mixture comprising an azeotropic or near-azeotropic composition of 1,1,1,2,2,3-hexafluoropropane and hydrogen fluoride, said process comprising:

(a) Subjecting said mixture to a first distillation step in which a composition enriched in either (i) hydrogen fluoride or (ii) 1,1,1,2,2,3-hexafluoropropane is removed as a first distillate composition with a first bottoms composition being enriched in the other of said components (i) or (ii); and (b) Subjecting said first distillate composition to a second distillation step conducted at a different pressure that the first distillation step in which the component enriched as a first bottoms composition in (a) is removed in a second distillate with a second bottoms composition enriched in the same component which was enriched in the first distillate composition.

Optionally, a first distillation step is carried out at a pressure that is greater than the second distillation step.

Further described is a process for the separation of 1,1,1,2,2-pentafluoro-3-chloropropane from a mixture comprising an azeotropic or near-azeotropic composition of 1,1,1,2,2-pentafluoro-3-chloropropane and hydrogen fluoride, said process comprising:

a) subjecting said mixture to a first distillation step in which a composition enriched in either (i) hydrogen fluoride or (ii) 1,1,1,2,2-pentafluoro-3-chloropropane is removed as a first distillate composition with a first bottoms composition being enriched in the other of said components (i) or (ii); and (a) subjecting said first distillate composition to a second distillation step conducted at a different pressure than the first distillation step in which the component enriched as first bottoms composition in (a) is removed in a second distillate composition with a second bottoms composition enriched in the same component which was enriched in the first distillate composition.

Optionally, the second distillation step is carried out at a pressure greater than the pressure of the first distillation step.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
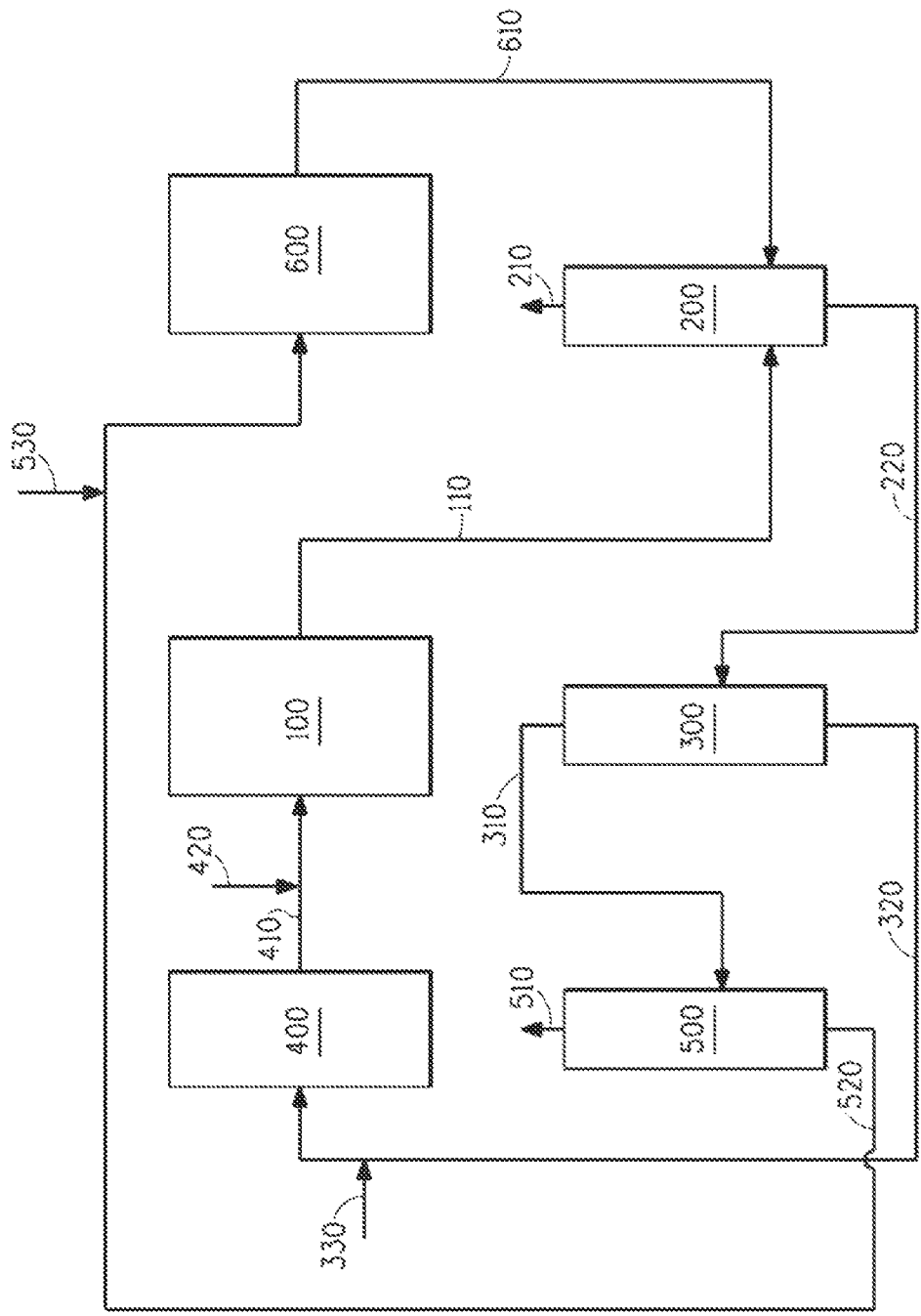
FIG. 1 is a schematic illustrating some embodiments of the process for making 3-chloro-1,1,1,2,2-pentafluoropropane (HCFC-235cb) or 1,1,1,2,2,3-hexafluoropropane (HFC-236cb).

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

As used herein, the term 2-fluorochloropropane refers to compounds of the formula $CCl_3CYFCH_2Cl$, wherein Y is F or Cl. Hence 2-fluorochloropropane refers to either 2-fluoro-1,1,1,2,3-pentachloropropane (HCFC-231bb), or to 2,2-difluoro-1,1,1,3-tetrachloropropane (HCFC-232cb). As used herein, partially fluorinate means to replace one, two, or three chlorine atoms of the $CCl_3$ group of the 2-fluorochloropropane with fluorine atoms to increase the fluorine content of the halogenated hydrocarbon, or to produce a mixture of such partially fluorinated 2-fluorochloropropanes. The degree of fluorination reflects the number of fluorine substituents that replace chlorine substituents in the $CCl3CYlFCH2Cl$ starting material and its converted products. For example, $CF_3CF_2CH_2Cl$ (HCFC-235cb) represents a higher degree of fluorination than $CCl3CClFCH2Cl$ (HCFC-231 bb)

As used herein, a fluorination catalyst is a catalyst which promotes the reaction whereby a fluorine atom is substituted for a chlorine atom in a halogenated hydrocarbon.

In one embodiment, the process is one to manufacture 3-chloro-1,1,1,2,2-pentafluoropropane (HCFC-235cb), an intermediate that may be converted into E- and Z-1,2,3,3,3-pentafluoro-1-propene (HFC-1225ye), a pentafluoropropene isomer of high interest as a low GWP refrigerant composition. HCFC-235cb may also be converted into 2,3,3,3-tetrafluoro-1-propene (HFC-1234yf), also of interest as a low GWP refrigerant.

In another embodiment, the process described is one to manufacture 1,1,1,2,2,3-hexafluoropropane (HFC-236cb), an intermediate readily converted into E- and Z-1,2,3,3,3-pentafluoro-1-propene (HFC-1225ye), a pentafluoropropene isomer of high interest as a low GWP refrigerant composition.

In one embodiment, 2-fluorochloropropanes such as 1,1,1,2,3-pentachloro-2-fluoropropane are fluorinated by reaction with HF in the reaction process set forth below:

  Halogen Exchange

  Halogen Exchange

  Halogen Exchange

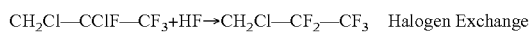  Halogen Exchange

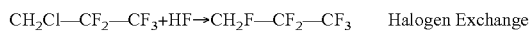  Halogen Exchange

Replacing multiple chlorine substituents in a 2-fluorochloropropane such as $CCl_3CClFCH_2Cl$ (HCFC-231 bb) with fluorine to produce HFC-236cb in a catalytic reactor can cause heat management problems. In some embodiments there is low equilibrium constant in the conversion of HCFC-235cb to HFC-236cb (see equation (1)).

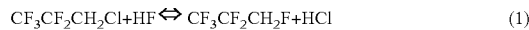 (1)

In some embodiments, in low equilibrium constant conversions, partially fluorinating a halogenated hydrocarbon precursor of the formula $CCl_3CYFCH_2Cl$, in a first step and completing the fluorination in a second, catalytic liquid phase fluorination is expected to reduce any inherent problems. In addition, in some embodiments, partially fluorinating $CCl_3CYFCH_2Cl$, to a mixture of intermediate halogenated hydrocarbons having a higher fluorine content gives a product that is thermally more stable than the pure $CCl_3CYFCH_2Cl$, with respect to tar formation. In addition, in some embodiments, by reducing the number of chlorine atoms to be exchanged in the second fluorination step the limitations introduced by the equilibrium in equation (1) are reduced.

The degree to which halogen exchange reactions proceed can be varied by varying the amount of HF and catalyst in combination as described herein below. In some embodiments, the halogen exchange reaction may be comprised of a first fluorination step wherein the pentachlorofluoropropane is contacted with HF in the absence of added catalyst, followed by a second fluorination step in the presence of a catalyst.

In some embodiments, the first fluorination step, starting 2-fluorochloropropane is contacted with HF in the gas phase or in the liquid phase at elevated temperature. In some embodiments, the first fluorination step is conducted in the liquid phase, heating a mixture of HF and 1,1,1,2,3-pentachloro-2-fluoropropane from room temperature to from about 100° C. to about 150° C. In some embodiments, the first fluorination time can be from about 15 minutes to about 4 hours. In some embodiments, the amount of HF relative to the amount of 2-fluorochloropropane may be from about 5 moles to about 50 moles of HF per mole of 2-fluorochloropropane. In other embodiments, the amount of HF relative to the amount of 2-fluorochloropropane may be from about 10 moles to about 30 moles of HF per mole of 2-fluorochloropropane. In some embodiments, hydrogen chloride is removed after the first fluorination step, prior to the second fluorination step.

The products of fluorination of 2-fluorochloropropane with HF may be used directly in the next step of the process or may be subjected to one of several purification schemes. In some embodiments, the reaction is carried out in such a way that the HCl produced during the fluorination of a 2-fluorochloropropane is removed via a distillation column present in the system. The same or a different distillation column may remove reaction products having the desired degree of fluorination from the reactor leaving unconverted 2-fluorochloropropane or products having a lower degree of fluorination in the reactor for further reaction. The fluorinated products removed from the reactor are then sent to a vaporizer or heated zone where they are brought to the desired temperature of the second step of the fluorination process. Alternatively, the entire reaction effluent formed by contacting a 2-fluorochloropropane with HF in the first reaction zone may be sent to a vaporizer or heated zone and then to the second fluorination step optionally with the further addition of HF.

In some embodiments, the second fluorination step is carried out in the liquid phase in the presence of a fluorination catalyst. In some embodiments, the second fluorination step is carried out in the vapor phase in the presence of a fluorination catalyst. In some embodiments, the fluorination catalyst is at least one selected from the group consisting of: $AlF_3$, BF$_3$, FeX$_3$, where X is the same or different and is selected from the group consisting of Cl and F, SbCl$_{3-x}$F$_x$ (x=0 to 3), AsF$_3$, MCl$_{5-y}$F$_y$ (wherein M is one of Sb, Nb, Ta or Mo, and y=0 to 5), M'Cl$_{4-z}$F$_z$ (wherein M' is one of Sn, Ti, Zr, Hf, and z=0 to 4), or mixtures thereof. In other embodiments, the fluorination catalyst is MCl$_{5-y}$F$_y$ (wherein M is one of Sb, Nb, Ta, and y=0 to 5) or mixtures thereof. Highly fluorinated catalysts such as for example, MF$_5$ when M=Nb or Ta and SbCl$_k$F$_{5-k}$ where k=0 to 3 may be conveniently prepared by fluorination of the chlorinated precursors, MCl$_5$ or SbCl$_5$, or SbCl$_3$+Cl$_2$, with HF either in the second fluorination reactor or in a separate fluorination step. In some embodiments, the FeX$_3$ is supported on carbon. In other embodiments, two or more fluorination catalyst can be used in the second fluorination step.

In some embodiments, to achieve the maximum degree of halogen exchange, at least 0.05 molar equivalent fluorination catalyst, based on the starting 2-fluorochloropropane is required. In other embodiments, to achieve the maximum degree of halogen exchange at least about 0.25 molar equivalents to about 5.0 molar equivalents of fluorination catalyst, based on the starting 2-fluorochloropropane is required. In yet other embodiments, a range of catalyst is from about 0.27 molar equivalents to about 4.0 molar equivalents.

In some embodiments, in the second fluorination step, total of the number of moles of HF added plus the total number of moles of available fluorine from the catalyst must be at least equal to 5. In another embodiment, the molar ratio of HF to the partially fluorinated pentachlorofluoropropane is from about 5 to about 50.

In some embodiments, the metal pentafluoride (prepared from, for example, Ta and Nb pentachlorides) can be prepared for use in some embodiments just prior to initiating the HF-2-fluorochloropropane reaction for the preparation of the desired polyfluorinated organic product.

Anhydrous or substantially anhydrous conditions means that water, which is detrimental to the reaction, should be excluded as much as possible from the reaction zone. The HF which is commercially available can be used in the reaction directly. Exclusion of moisture from the reaction vessel by means of appropriate moisture traps, inert gas purging, etc., is a routine procedure and is well known in the art.

In some embodiments, the second fluorination step can be carried out in a batchwise manner in the liquid phase at from about 0° C. to about 175° C. In another embodiment, the second fluorination step is carried out at from about 60° C. to about 160° C. At reaction temperatures below these limits the reactions become too slow to be useful, and at temperature above these limits the yields of products are lowered by side reactions and polymerization. In yet other embodiments, the second fluorination step in carried out in a continuous manner.

The reaction vessel is constructed from materials which are resistant to the action of hydrogen fluoride. Examples include stainless steels, high nickel alloys such as monel, "Hastelloy" and "Inconel", and plastics such as polyethylene, polypropylene, polychlorotrifluoroethylene and polytetrafluoroethylene. The high nickel alloys are preferred because of the superacidities of some fluorination catalysts in combination with liquid HF. For reactions at a temperature either below the boiling point of hydrogen fluoride (19.5° C.) or below the boiling point of the most volatile reactant, the reaction vessel can be closed or open to the atmosphere if provisions to exclude moisture are taken. For reactions at a temperature at or above the boiling point of hydrogen fluoride or the most volatile component, a closed vessel or a pressure-regulated partially open reaction is used to minimize the loss of the reactants.

In some embodiments, pressure is not critical. In other embodiments, the process is preformed at atmospheric and autogenous pressures. Means can be provided for the venting of the excess pressure of hydrogen chloride formed in the substitution reaction and can offer an advantage in minimizing the formation of side products.

In some embodiments, the reactions are conducted by introducing the reagent in any order into the reaction vessel. The first fluorination step may be conducted first in one reaction vessel, and then the contents transferred to a second vessel with catalyst. In other embodiments, the first fluorination and the catalyzed fluorination step can be conducted in the same reaction vessel. In other embodiments, in batch-type autogenous pressure operation, the catalyst and starting material are placed in the reaction vessel which is then cooled, and the required amount of hydrogen fluoride is condensed in the vessel. The vessel may be cooled in dry Ice or liquid nitrogen and evacuated prior to the introduction of hydrogen fluoride to facilitate the hydrogen fluoride addition. The contents of the vessel are raised to the appropriate reaction temperature and agitated by shaking or stirring for a length of time sufficient to cause the reaction to occur. The reaction times can be from about 1 to about 17 hours. In other embodiments, the reaction times may be from about 1 to about 6 hours.

In other embodiments, the fluorination reaction can be conducted in a continuous or semi-continuous manner with HF and the halocarbon starting material fed continuously or intermittently to a first reaction vessel, and from there to a second reaction vessel containing the fluorination catalyst at a temperature and pressure effective to result in the fluorination of the starting material to the desired polyfluorinated product. In other embodiments, the temperature and pressure are such that the desired product is in the gaseous state, so that a reaction product stream can be removed continuously or intermittently from the reaction zone. In other embodiments, the pressure within the reactor can be controlled by means of a pressure regulator, and the temperature of the reaction product stream can be controlled, if desired, by use of a condenser/dephlegmator, all these techniques being well known to the art.

In some embodiments, the reaction of HF with partially fluorinated 2-fluorochloropropane in the presence of at least one fluorination catalyst and can be conducted in the presence of a diluent which may be a high boiling inert liquid, e.g., a perfluorinated hydrocarbon, or the desired reaction product itself, CF$_3$CF$_2$CH$_2$X, wherein X=F or Cl.

In some embodiments, for the preparation of 1,1,1,2,2,3-hexafluoropropane, and the isolation of 1,1,1,2,2,3-hexafluoropropane, the 1,1,1,2,2,3-hexafluoropropane forms an azeotrope with HF.

In some embodiments, provided is a composition, which comprises 1,1,1,2,2,3-hexafluoropropane and an effective amount of hydrogen fluoride (HF) to form an azeotropic composition. By effective amount is meant an amount, which, when combined with 1,1,1,2,2,3-hexafluoropropane, results in the formation of an azeotropic or near-azeotropic mixture.

Compositions may be formed that comprise azeotropic combinations of hydrogen fluoride with 1,1,1,2,2,3-hexafluoropropane. In some embodiments, these include compositions comprising from about 36.9 mole percent to about 55.1 mole percent HF and from about 63.1 mole percent to about 44.9 mole percent 1,1,1,2,2,3-hexafluoropropane (which forms an azeotrope boiling at a temperature from between about −6.1° C. and about 108° C. and at a pressure from between about 15 psi and about 490 psia).

In other embodiments, near-azeotropic compositions containing HF and 1,1,1,2,2,3-hexafluoropropane may also be formed. Such near-azeotropic compositions comprise about 38 mole percent to about 75.8 mole percent 1,1,1,2,2,3-hexafluoropropane and about 24.2 mole percent to about 62 mole percent HF at temperatures ranging from about −20° C. to about 120° C. and at pressures from about 8 psi to about 389 psi.

In other embodiments, compositions may be formed that consist essentially of azeotropic combinations of hydrogen fluoride with 1,1,1,2,2,3-hexafluoropropane. These include compositions consisting essentially of from about 36.9 mole percent to about 55.1 mole percent HF and from about 63.1 mole percent to about 44.9 mole percent 1,1,1,2,2,3-hexafluoropropane (which forms an azeotrope boiling at a temperature from between about −6.1° C. and about 108° C. and at a pressure from between about 15 psi and about 490 psi.

In other embodiments, near azeotropic compositions may also be formed that consist essentially of about 38 mole percent to about 75.8 mole percent 1,1,1,2,2,3-hexafluoropropane and about 24.2 mole percent to about 62 mole percent HF at temperatures ranging from about −20° C. to about 120° C. and at pressures from about 8 psi to about 389 psi.

In considering a process for the preparation of 1,1,1,2,2-pentafluoro-3-chloropropane, and the isolation of 1,1,1,2,2-pentafluoro-3-chloropropane from such a process, it has been discovered surprisingly that the 1,1,1,2,2-pentafluoro-3-chloropropane forms an azeotrope with HF.

In some embodiments, provided is a composition, which comprises 1,1,1,2,2-pentafluoro-3-chloropropane and an effective amount of hydrogen fluoride (HF) to form an azeotropic composition. By effective amount is meant an amount, which, when combined with 1,1,1,2,2-pentafluoro-3-chloropropane, results in the formation of an azeotropic or near-azeotropic mixture.

Compositions may be formed that comprise azeotropic combinations of hydrogen fluoride with 1,1,1,2,2-pentafluoro-3-chloropropane. In some embodiments, these include compositions comprise from about 65.1 mole percent to about 82.7 mole percent HF and from about 34.9 mole percent to about 17.3 mole percent 1,1,1,2,2-pentafluoro-3-chloropropane (which forms an azeotrope boiling at a temperature from between about 8.2° C. and about 127.1° C. and at a pressure from between about 15 psi and about 480 psi.

In other embodiments, near-azeotropic compositions containing HF 1,1,1,2,2-pentafluoro-3-chloropropane may also be formed. Such near-azeotropic compositions comprise about 11.4 mole percent to about 38.8 mole percent 1,1,1,2, 2-pentafluoro-3-chloropropane and about 61.2 mole percent to about 88.6 mole percent HF at temperatures ranging from about −20° C. to about 120° C. and at pressures from about 4.2 psi to about 245.6 psi.

It should be understood that while an azeotropic or near-azeotropic composition may exist at a particular ratio of the components at given temperatures and pressures, the azeotropic composition may also exist in compositions containing other components. These additional components include the individual components of the azeotropic composition, said components being present as an excess above the amount being present as the azeotropic composition. For instance, the azeotrope of 1,1,1,2,2-pentafluoro-3-chloropropane and HF may be present in a composition that has an excess of 1,1,1, 2,2-pentafluoro-3-chloropropane, meaning that the azeotropic composition is present and additional 1,1,1,2,2-pentafluoro-3-chloropropane is also present.

In other embodiments, compositions may be formed that consist essentially of azeotropic combinations of hydrogen fluoride with 1,1,1,2,2-pentafluoro-3-chloropropane. These include compositions consisting essentially of from about 65.1 mole percent to about 82.7 mole percent HF and from about 17.3 mole percent to about 34.9 mole percent 1,1,1,2, 2-pentafluoro-3-chloropropane (which forms an azeotrope boiling at a temperature from between about 8.2° C. and about 127.1° C. and at a pressure from between about 15 psi and about 480 psi).

In yet other embodiments, near azeotropic compositions may also be formed that consist essentially of about 11.4 mole percent to about 38.8 mole percent 1,1,1,2,2-pentafluoro-3-chloropropane and about 61.2 mole percent to about 88.6 mole percent HF at temperatures ranging from about −20° C. to about 120° C. and at pressures from about 4.2 psi to about 245.6 psi.

At atmospheric pressure, the boiling points of hydrofluoric acid and 1,1,1,2,2,3-hexafluoropropane are about 19.5° C. and about −1° C., respectively.

In some embodiments, the HF/1,1,1,2,2,3-hexafluoropropane azeotropic and near-azeotropic compositions are useful in processes to produce 1,1,1,2,2,3-hexafluoropropane and in processes to purify 1,1,1,2,2,3-hexafluoropropane The HF/1, 1,1,2,2,3-hexafluoropropane azeotropic and near-azeotropic compositions may be useful in any process that creates a composition containing 1,1,1,2,2,3-hexafluoropropane and HF.

In some embodiments, azeotropic distillation with hydrogen fluoride may be carried out to separate 1,1,1,2,2,3-hexafluoropropane from HCFC-235cb. HCFC-235cb may be converted to HFC-236cb by fluorination as disclosed herein. A two-column pressure-swing distillation may then be carried out to separate the HF from the desired 1,1,1,2,2,3-hexafluoropropane product. And in other embodiments, two-column pressure-swing distillation may be carried out to separate HF from HCFC-235cb. HF may also be removed from the halogenated hydrocarbon components of the product mixture using, for example, standard aqueous solution scrubbing techniques. However, the production of substantial amounts of scrubbing discharge can create aqueous waste disposal concerns. Thus, there remains a need for processes recovering HF from such product mixtures.

While the initial mixture treated in accordance with the processes disclosed herein can be obtained from a variety of sources, including by adding 1,1,1,2,2,3-hexafluoropropane to HF-containing compositions, in one embodiment, an advantageous use of the disclosed processes resides in treating the effluent mixtures from the preparation of 1,1,1,2,2,3-hexafluoropropane.

In some embodiments, another aspect provides a process for the separation of 1,1,1,2,2,3-hexafluoropropane from HCFC-235cb comprising: a) forming a mixture of 1,1,1,2,2, 3-hexafluoropropane, HCFC-235cb, and hydrogen fluoride; and b) subjecting said mixture to a distillation step forming a column distillate composition comprising an azeotropic or near-azeotropic composition of HF and 1,1,1,2,2,3-hexafluoropropane essentially free of HCFC-235cb, as an overhead stream. In some embodiments, a bottoms stream from such a distillation comprises HCFC-235cb. In other embodiments, a bottoms stream from such a distillation comprises HCFC-235cb and hydrogen fluoride.

Use of the term "essentially free of HCFC-235cb" means that the composition contains less than about 100 ppm HCFC-235cb (on a mole basis). In other embodiments, "essentially free of HCFC-235cb" means that the composition contains less than about 10 ppm HCFC-235cb (mole basis). In yet other embodiments, "essentially free of HCFC-235cb" means that the composition contains less than about 1 ppm, of HCFC-235cb (mole basis).

This azeotropic/near azeotropic distillation takes advantage of the low boiling azeotropic and near azeotropic compositions formed by 1,1,1,2,2,3-hexafluoropropane and HF. The azeotropic composition boils at a temperature lower than the boiling point of either pure component and lower than the boiling point of HCFC-235cb as well.

As stated previously, the mixture of 1,1,1,2,2,3-hexafluoropropane, HCFC-235cb and HF may be formed by any practical means. In some embodiment, the disclosed process is useful for the separation of 1,1,1,2,2,3-hexafluoropropane from the reaction mixture produced by the fluorination of HCFC-231bb. The reaction mixture produced may then be treated by the instant process to remove HCFC-235cb. The 1,1,1,2,2,3-hexafluoropropane is taken overhead as the distillate from the distillation column as an azeotropic or near-azeotropic composition of 1,1,1,2,2,3-hexafluoropropane with HF. The HCFC-235cb is taken out of the bottom of the column as a bottoms composition and may contain some amount of HF, as well. The amount of HF in the HCFC-235cb from the bottom of the distillation column may vary from about 35 mole percent to less than 1 part per million (ppm, mole basis) depending on the manner in which the fluorination reaction is conducted. In fact, if the fluorination reaction is conducted in a manner to provide 50 percent conversion of the HCFC-235cb and the reaction mixture leaving the reaction zone is fed directly to the distillation step, the HCFC-235cb leaving the bottom of the distillation process will contain about 34 mole percent HF.

In some embodiments, operating the disclosed azeotropic distillation involves providing an excess of 1,1,1,2,2,3-hexafluoropropane to the distillation column. If the proper amount of 1,1,1,2,2,3-hexafluoropropane is fed to the column, then all the HF may be taken overhead as an azeotropic composition containing 1,1,1,2,2,3-hexafluoropropane and HF. Thus, the HCFC-235cb removed from the column bottoms will be essentially free of HF.

Use of the term "essentially free of HF" means that the HF is present in an amount less than about 100 ppm HF (on a mole basis). In some embodiments, essentially free of HF means that HF is present in amounts less than 10 ppm (mole basis); and, in other embodiments, essentially free of HF means that HF is present in amounts less than 1 ppm (mole basis).

In some embodiments, in the distillation step, the distillate exiting the distillation column overhead comprising HF and 1,1,1,2,2,3-hexafluoropropane may be condensed using, for example, standard reflux condensers. At least a portion of this condensed stream may be returned to the top of the column as reflux. The ratio of the condensed material, which is returned to the top of the distillation column as reflux, to the material removed as distillate is commonly referred to as the reflux ratio. The specific conditions which may be used for practicing the distillation step depend upon a number of parameters, such as the diameter of the distillation column, feed points, and the number of separation stages in the column, among others. The operating pressure of the distillation column may range from about 10 psi pressure to about 200 psi (1380 kPa), normally about 20 psi to about 50 psi. In some embodiments, the distillation column is operated at a pressure of about 25 psi (172 kPa) with a bottoms temperature of about 44° C. and a top temperature of about 6° C. Normally, increasing the reflux ratio results in increased distillate stream purity, but generally the reflux ratio ranges between 1/1 to 200/1. The temperature of the condenser, which is located adjacent to the top of the column, is normally sufficient to substantially condense the distillate that is exiting from the top of the column, or is that temperature required to achieve the desired reflux ratio by partial condensation.

In some embodiments, the column distillate composition comprising an azeotropic or near-azeotropic composition of HF and 1,1,1,2,2,3-hexafluoropropane, essentially free of HCFC-235cb, must be treated to remove the HF and provide pure 1,1,1,2,2,3-hexafluoropropane as product. This may be accomplished, for example, by neutralization or by a second distillation process, as described herein.

In some embodiments, a further aspect provides a process for the separation of 1,1,1,2,2,3-hexafluoropropane from a mixture comprising an azeotropic or near-azeotropic composition of 1,1,1,2,2,3-hexafluoropropane and HF, said process comprising: a) subjecting said mixture to a first distillation step in which a composition enriched in either (i) hydrogen fluoride or (ii) 1,1,1,2,2,3-hexafluoropropane is removed as a first distillate composition with a first bottoms composition being enriched in the other of said components (i) or (ii); and b) subjecting said first distillate composition to a second distillation step conducted at a different pressure than the first distillation step in which the component enriched in the first bottoms composition in (a) is removed in a second distillate composition with a second bottoms composition enriched in the same component which was enriched in the first distillate composition.

The process as described above takes advantage of the change in azeotrope composition at different pressures to effect the separation of 1,1,1,2,2,3-hexafluoropropane and HF. In one embodiment, the first distillation step is carried out at a higher pressure relative to the second distillation step. At higher pressures, the HF/1,1,1,2,2,3-hexafluoropropane azeotrope contains more 1,1,1,2,2,3-hexafluoropropane, or less HF. Thus, this high-pressure distillation step produces an excess of HF, which boiling at a higher temperature than the azeotrope will exit the column as the bottoms as essentially pure HF. The first column distillate is then fed to a second distillation step operating at lower pressure. At the lower pressure, the HF/1,1,1,2,2,3-hexafluoropropane azeotrope shifts to lower concentrations of 1,1,1,2,2,3-hexafluoropropane. Therefore, in this second distillation step, there exists an excess of 1,1,1,2,2,3-hexafluoropropane. The excess 1,1,1,2,2,3-hexafluoropropane, having a boiling point higher than the azeotrope, exits the second distillation column as the bottoms composition. The disclosed process may be conducted in such as manner as to produce 1,1,1,2,2,3-hexafluoropropane essentially free of HF. Additionally, the disclosed process may be conducted in such a manner as to produce HF essentially free of 1,1,1,2,2,3-hexafluoropropane.

In other embodiments, the first distillation step is carried out at a lower pressure relative to the second distillation step. At lower pressures, the HF/1,1,1,2,2,3-hexafluoropropane azeotrope contains less 1,1,1,2,2,3-hexafluoropropane. Thus, this low-pressure distillation step produces an excess of 1,1,1,2,2,3-hexafluoropropane, which boiling at a higher temperature than the azeotrope will exit the column as the bottoms as essentially pure 1,1,1,2,2,3-hexafluoropropane. The first column distillate is then fed to a second distillation step operating at higher pressure. At the higher pressure, the HF/1,1,1,2,2,3-hexafluoropropane azeotrope shifts to higher concentrations of 1,1,1,2,2,3-hexafluoropropane, or lower concentrations of HF. Therefore, in this second distillation step, there exists an excess of HF. The excess HF, having a boiling point higher than the azeotrope, exits the second distillation column as the bottoms composition. The disclosed process may be conducted in such as manner as to produce 1,1,1,2,2,3-hexafluoropropane essentially free of HF. Additionally, the disclosed process may be conducted in such a manner as to produce HF essentially free of 1,1,1,2,2,3-hexafluoropropane.

Use of the term "essentially free of 1,1,1,2,2,3-hexafluoropropane" means that the composition contains less than about 100 ppm 1,1,1,2,2,3-hexafluoropropane (on a mole basis). In another embodiment, "essentially free of 1,1,1,2,2,3-hexafluoropropane" means that the composition contains less than about 10 ppm 1,1,1,2,2,3-hexafluoropropane (mole basis). In yet other embodiments, "essentially free of 1,1,1,2,2,3-hexafluoropropane" means that the composition contains less than about 1 ppm, of 1,1,1,2,2,3-hexafluoropropane (mole basis). In some embodiments of the process, the HCFC-235cb/HF mixture, or HFCF-235cb separated from the HFC-236cb/HF azeotrope is fed to a separate liquid phase fluorination reactor to convert the HCFC-235cb to HFC-236cb.

In some embodiments, the HF/1,1,1,2,2-pentafluoro-3-chloropropane azeotropic and near-azeotropic compositions are useful in processes to produce 1,1,1,2,2-pentafluoro-3-chloropropane and in processes to purify 1,1,1,2,2-pentafluoro-3-chloropropane. In fact, the HF/1,1,1,2,2-pentafluoro-3-chloropropane azeotropic and near-azeotropic compositions may be useful in any process that creates a composition containing 1,1,1,2,2-pentafluoro-3-chloropropane and HF.

In some embodiments, azeotropic distillation with hydrogen fluoride may be carried out to separate 1,1,1,2,2-pentafluoro-3-chloropropane from partially fluorinated 2-fluorochloropropanes. Partially fluorinated 2-fluorochloropropanes may be converted to HCFC-235cb by fluorination as disclosed herein. A two-column pressure-swing distillation may then be carried out to separate the HF from the desired 1,1,1,2,2-pentafluoro-3-chloropropane product. HF may also be removed from the halogenated hydrocarbon components of the product mixture using, for example, standard aqueous solution scrubbing techniques. However, the production of substantial amounts of scrubbing discharge can create aqueous waste disposal concerns. Thus, there remains a need for processes recovering HF from such product mixtures.

While the initial mixture treated in accordance with the processes disclosed herein can be obtained from a variety of sources, including by adding 1,1,1,2,2-pentafluoro-3-chloropropane to HF-containing compositions, in one embodiment, an advantageous use of the disclosed processes resides in treating the effluent mixtures from the preparation of 1,1,1,2,2-pentafluoro-3-chloropropane.

In some embodiments, another aspect provides a process for the separation of 1,1,1,2,2-pentafluoro-3-chloropropane from partially fluorinated 2-fluorochloropropanes comprising: a) forming a mixture of 1,1,1,2,2-pentafluoro-3-chloropropane, partially fluorinated 2-fluorochloropropanes, and hydrogen fluoride; and b) subjecting said mixture to a distillation step forming a column distillate composition comprising an azeotropic or near-azeotropic composition of HF and 1,1,1,2,2-pentafluoro-3-chloropropane essentially free of partially fluorinated 2-fluorochloropropanes, as an overhead stream. In one embodiment, a bottoms stream from such a distillation comprises partially fluorinated 2-fluorochloropropanes. In another embodiment, a bottoms stream from such a distillation comprises partially fluorinated 2-fluorochloropropanes and hydrogen fluoride.

Use of the term "essentially free of partially fluorinated 2-fluorochloropropanes" means that the composition contains less than about 100 ppm partially fluorinated 2-fluorochloropropanes (mole basis). In other embodiments, "essentially free of partially fluorinated 2-fluorochloropropanes" means that the composition contains less than about 10 ppm partially fluorinated 2-fluorochloropropanes (mole basis). In yet other embodiments, "essentially free of partially fluorinated 2-fluorochloropropanes" means that the composition contains less than about 1 ppm, of partially fluorinated 2-fluorochloropropanes (mole basis).

This azeotropic distillation takes advantage of the low boiling azeotropic composition formed by 1,1,1,2,2-pentafluoro-3-chloropropane and HF. The azeotropic composition boils at a temperature lower than the boiling point of either pure component and lower than the boiling point of partially fluorinated 2-fluorochloropropanes as well.

As stated previously, the mixture of 1,1,1,2,2-pentafluoro-3-chloropropane, partially fluorinated 2-fluorochloropropanes and HF may be formed by any practical means. In some embodiments, the disclosed process is particularly useful for the separation of 1,1,1,2,2-pentafluoro-3-chloropropane from the reaction mixture produced by the fluorination of HCFC-231bb. The reaction mixture produced may then be treated by the instant process to remove partially fluorinated 2-fluorochloropropanes. The 1,1,1,2,2-pentafluoro-3-chloropropane is taken overhead as the distillate from the distillation column as an azeotropic or near-azeotropic composition of 1,1,1,2,2-pentafluoro-3-chloropropane with HF. The partially fluorinated 2-fluorochloropropanes is taken out of the bottom of the column as a bottoms composition and may contain some amount of HF, as well. The amount of HF in the partially fluorinated 2-fluorochloropropanes from the bottom of the distillation column may vary from about 35 mole percent to less than 1 part per million (ppm, mole basis) depending on the manner in which the fluorination reaction is conducted. In fact, if the fluorination reaction is conducted in a manner to provide 50 percent conversion of the partially fluorinated 2-fluorochloropropanes and the reaction mixture leaving the reaction zone is fed directly to the distillation step, the partially fluorinated 2-fluorochloropropanes leaving the bottom of the distillation process will contain about 34 mole percent HF.

In some embodiments, operating the disclosed azeotropic distillation involves providing an excess of 1,1,1,2,2-pentafluoro-3-chloropropane to the distillation column. If the proper amount of 1,1,1,2,2-pentafluoro-3-chloropropane is fed to the column, then all the HF may be taken overhead as an azeotropic composition containing 1,1,1,2,2-pentafluoro-3-chloropropane and HF. Thus, the partially fluorinated 2-fluorochloropropanes removed from the column bottoms will be essentially free of HF.

In some embodiments, in the distillation step, the distillate exiting the distillation column overhead comprising HF and 1,1,1,2,2-pentafluoro-3-chloropropane may be condensed using, for example, standard reflux condensers. At least a portion of this condensed stream may be returned to the top of the column as reflux. The ratio of the condensed material, which is returned to the top of the distillation column as reflux, to the material removed as distillate is commonly referred to as the reflux ratio. The specific conditions which may be used for practicing the distillation step depend upon a number of parameters, such as the diameter of the distillation column, feed points, and the number of separation stages in the column, among others. The operating pressure of the distillation column may range from about 10 psi pressure to about 200 psi (1380 kPa), normally about 20 psi to about 50 psi. In one embodiment, the distillation column is operated at a pressure of about 25 psi (172 kPa) with a bottoms temperature of about 44° C. and a top temperature of about 6° C. Normally, increasing the reflux ratio results in increased distillate stream purity, but generally the reflux ratio ranges between 1/1 to 200/1. The temperature of the condenser, which is located adjacent to the top of the column, is normally sufficient to substantially condense the distillate that is exiting from the top of the column, or is that temperature required to achieve the desired reflux ratio by partial condensation.

In some embodiments, the column distillate composition comprising an azeotropic or near-azeotropic composition of HF and 1,1,1,2,2-pentafluoro-3-chloropropane, essentially free of partially fluorinated 2-fluorochloropropanes, must be treated to remove the HF and provide pure 1,1,1,2,2-pentafluoro-3-chloropropane as product. This may be accomplished, for example, by neutralization or by a second distillation process, as described herein.

In some embodiments, a further aspect provides a process for the separation of 1,1,1,2,2-pentafluoro-3-chloropropane from a mixture comprising an azeotropic or near-azeotropic composition of 1,1,1,2,2-pentafluoro-3-chloropropane and HF, said process comprising: a) subjecting said mixture to a first distillation step in which a composition enriched in either (i) hydrogen fluoride or (ii) 1,1,1,2,2-pentafluoro-3-chloropropane is removed as a first distillate composition with a first bottoms composition being enriched in the other of said components (i) or (ii); and b) subjecting said first distillate composition to a second distillation step conducted at a different pressure than the first distillation step in which the component enriched in the first bottoms composition in (a) is removed in a second distillate composition with a second bottoms composition enriched in the same component which was enriched in the first distillate composition.

The process as described above takes advantage of the change in azeotrope composition at different pressures to effect the separation of 1,1,1,2,2-pentafluoro-3-chloropropane and HF. In some embodiments, the first distillation step is carried out at a higher pressure relative to the second distillation step. At higher pressures, the HF/1,1,1,2,2-pentafluoro-3-chloropropane azeotrope contains more 1,1,1,2,2-pentafluoro-3-chloropropane, or less HF. Thus, this high-pressure distillation step produces an excess of HF, which boiling at a higher temperature than the azeotrope will exit the column as the bottoms as essentially pure HF. The first column distillate is then fed to a second distillation step operating at lower pressure. At the lower pressure, the HF/1,1,1,2,2-pentafluoro-3-chloropropane azeotrope shifts to lower concentrations of 1,1,1,2,2-pentafluoro-3-chloropropane. Therefore, in this second distillation step, there exists an excess of 1,1,1,2,2-pentafluoro-3-chloropropane. The excess 1,1,1,2,2-pentafluoro-3-chloropropane, having a boiling point higher than the azeotrope, exits the second distillation column as the bottoms composition. The disclosed process may be conducted in such as manner as to produce 1,1,1,2,2-pentafluoro-3-chloropropane essentially free of HF. Additionally, the disclosed process may be conducted in such a manner as to produce HF essentially free of 1,1,1,2,2-pentafluoro-3-chloropropane.

In other embodiments, the first distillation step is carried out at a lower pressure relative to the second distillation step. At lower pressures, the HF/1,1,1,2,2-pentafluoro-3-chloropropane azeotrope contains less 1,1,1,2,2-pentafluoro-3-chloropropane. Thus, this low-pressure distillation step produces an excess of 1,1,1,2,2-pentafluoro-3-chloropropane, which boiling at a higher temperature than the azeotrope will exit the column as the bottoms as essentially pure 1,1,1,2,2-pentafluoro-3-chloropropane. The first column distillate is then fed to a second distillation step operating at higher pressure. At the higher pressure, the HF/1,1,1,2,2-pentafluoro-3-chloropropane azeotrope shifts to higher concentrations of 1,1,1,2,2-pentafluoro-3-chloropropane, or lower concentrations of HF. Therefore, in this second distillation step, there exists an excess of HF. The excess HF, having a boiling point higher than the azeotrope, exits the second distillation column as the bottoms composition. The disclosed process may be conducted in such as manner as to produce 1,1,1,2,2-pentafluoro-3-chloropropane essentially free of HF. Additionally, the disclosed process may be conducted in such a manner as to produce HF essentially free of 1,1,1,2,2-pentafluoro-3-chloropropane.

Use of the term "essentially free of 1,1,1,2,2-pentafluoro-3-chloropropane" means that the composition contains less than about 100 ppm 1,1,1,2,2-pentafluoro-3-chloropropane (mole basis). In other embodiments, "essentially free of 1,1,1,2,2-pentafluoro-3-chloropropane" means that the composition contains less than about 10 ppm 1,1,1,2,2-pentafluoro-3-chloropropane (mole basis). In yet other embodiments, "essentially free of 1,1,1,2,2-pentafluoro-3-chloropropane" means that the composition contains less than about 1 ppm of 1,1,1,2,2-pentafluoro-3-chloropropane (on a mole basis). In some embodiments of the process, the partially fluorinated 2-fluorochloropropanes/HF mixture, or HFCF-235cb separated from the HCFC-235cb/HF azeotrope is fed to a separate liquid phase fluorination reactor to convert the partially fluorinated 2-fluorochloropropanes to HCFC-235cb.

The preparation of 1,1,1,2,3-pentachloro-2-fluoropropane (HCFC-231 bb) from 1,2-dichloro-2-fluoropropane (HCFC-261 ba) is disclosed by Henne in the Journal of the American Chemical Society volume 63, 2692-2694, 1941, the disclosure of which is herein incorporated by reference.

The preparation of 1,1,1,3-tetrachloro-2,2-difluoropropane (HCFC-232cb) from 2,2-difluoropropane (HFC-272ca) is disclosed by Henne in the Journal of the American Chemical Society volume 59, 2434-2436, 1937, the disclosure of which is herein incorporated by reference.

DETAILED DESCRIPTION OF THE FIGURES

FIG. 1 is a schematic illustrating one method making 3-chloro-1,1,1,2,2-pentafluoropropane (HCFC-235cb) or 1,1,1,2,2,3-hexafluoropropane (HFC-236cb).

Stream 420 (may be 1,1,1,2,3-pentachloro-2-fluoropropane (HCFC-231 bb), is fed to the first reactor, 100, along with the output from the second reactor, 400, which is the output stream, 410. The reactor 400 comprises partially fluorinated 2-fluorochloropropanes plus additional HF, 330. Reactor 100 is the reactor for the first fluorination step. Reactor 100 lacks a catalyst. This reactor may be a liquid phase reactor or a vapor phase reactor. The output of reactor 100, stream 110, may comprise partially fluorinated 2-fluorochloropropanes, HCFC-235cb, HFC 236cb, hydrogen fluoride and hydrogen chloride and mixtures of two or more thereof.

Stream 110 proceeds to a separation column 200, wherein hydrogen chloride, 210, is removed as an overhead stream. Column 200 also receives stream 610, which is the output stream from reactor 600 and described more fully below. Bottom stream, 220, may comprise partially fluorinated chloropropanes, such as partially fluorinated HCFC-231 bb, HCFC-235cb, HCFC-236cb, hydrogen fluoride and mixtures of two or more thereof.

Stream 220 is then fed to a separation column, 300. The overhead steam, 310, from column 300 may comprises partially fluorinated 2-fluorochloropropanes, HCFC-235cb, HFC-236cb, hydrogen fluoride and mixtures of two or more. The bottom stream from column 300, stream 320, is then fed to second reactor, 400, along with additional hydrogen fluoride, 330. Stream 320 comprises chlorofluoropropanes and hydrogen fluoride. Reactor 400 is the reactor for the second fluorination step and contains at least one catalyst.

The overhead stream from column 300, stream 310, which is fed to separation column 500 to separate out the HFC-236cb/HF azeotrope/near-azeotropic if present as an overhead stream, 510, and a partially fluorinated 2-fluorochloropropanes/HF mixture and/or the HCFC-235cb/HF azeotrope/near-azeotrope mixtures comprise bottom stream, 520. If HFC-236cb is not present, the overhead stream 510 comprises the HCFC-235cb/HF azeotrope/near-azeotrope mixture at the pressure at which column 500 is operated at. Bottom stream, 520, comprise partially fluorinated 2-fluorochloropropanes The bottom stream, 520, is then fed to another second fluorination step reactor, 600, which also has at least one catalyst which can be the same or different from the catalyst in reactor 400, and along with additional hydrogen fluoride, 530, to provide an output stream, 610, may comprising HCFC-235cb, HFC 236cb, partially fluorinated 2-fluorochloropropanes, hydrogen fluoride and hydrogen chloride. Output stream, 610 is fed to separation column 200.

Stream 510 can be separated further if desired, by using known separation techniques such as HF scrubbers or by using a multicolumn pressure swing distillation process.

Figure 2:
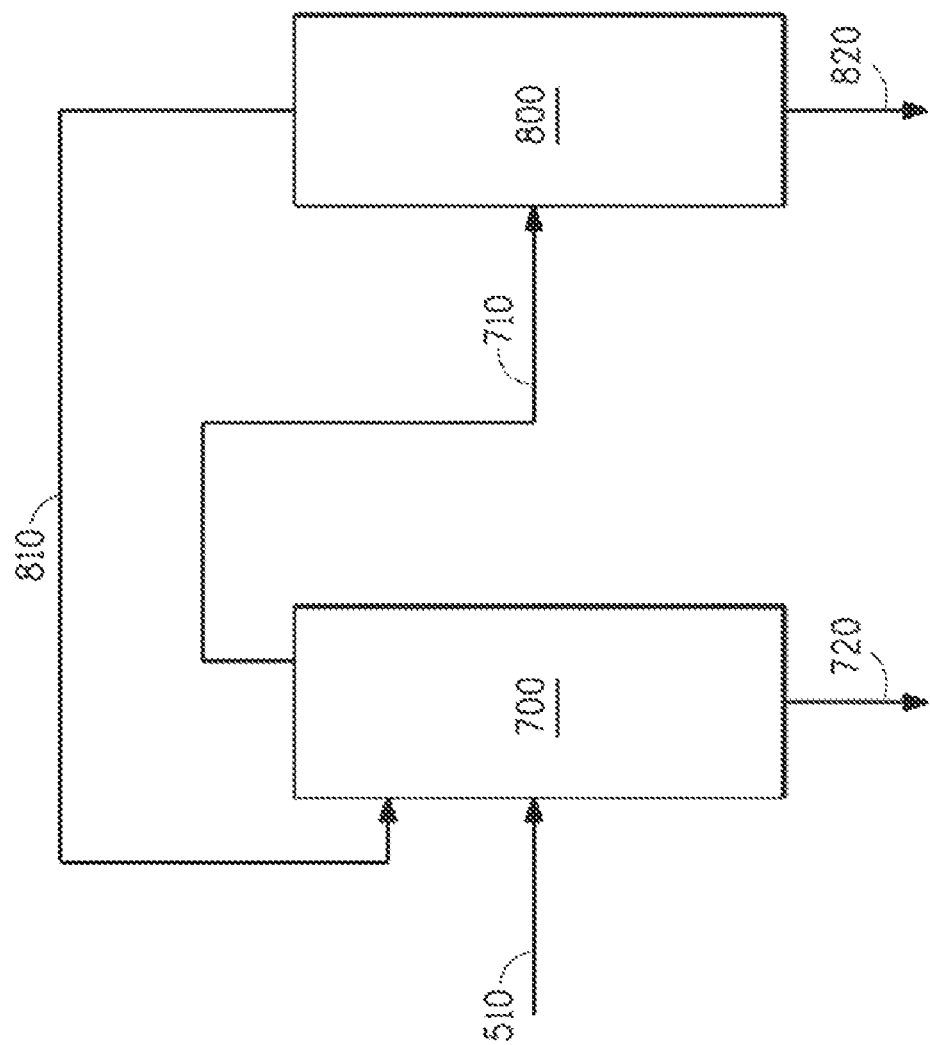
FIG. 2 is a schematic illustrating a two column pressure swing distillation process for separating 3-chloro-1,1,1,2,2-pentafluoropropane (HCFC-235cb) or 1,1,1,2,2,3-hexafluoropropane (HFC-236cb) from HF.

FIG. 2 is a schematic illustrating a two column pressure swing distillation process for separating 3-chloro-1,1,1,2,2-pentafluoropropane (HCFC-235cb) or 1,1,1,2,2,3-hexafluoropropane (HFC-236cb) from HF. In FIG. 2, stream 510 (described above) is fed into a first distillation column 700 which is operated at a first pressure and a first temperature; overhead stream 710 is an azeotrope of the (HCFC-235cb) or (HFC-236cb) and HF, respectively, depending on the feed. The azeotrope compositions depends on the pressure at which the column 700 is operated. Overhead stream 710 which feeds into a second distillation column 800, which is operated at a second pressure and a second temperature (which may be higher or lower than the first pressure and first temperature of column 700); output stream 720 is the bottom stream from the distillation column 700, and can be essentially pure HF, HCFC 235cb, or HFC 236cb depending on the operating conditions of the column. Column 800 is a distillation column which can be the same or different from column 700. Column 700 and Column 800 are operated at different pressures. Stream 810 is the overhead stream and is an azeotrope of the (HCFC-235cb) or (HFC-236cb) and HF, respectively, depending on the feed stream. Stream 820 is the output stream from the distillation column 800, and can be essentially pure HF, HCFC 235cb, or HFC 236cb depending on the operating conditions of the column. The distillation columns illustrated in FIGS. 1 and 2 can be multistage and can have up to and including 20 theoretical stages.

As used herein, an azeotropic composition is a constant boiling liquid admixture of two or more substances wherein the admixture distills without substantial composition change and behaves as a constant boiling composition. Constant boiling compositions, which are characterized as azeotropic, exhibit either a maximum or a minimum boiling point, as compared with that of the non-azeotropic mixtures of the same substances. Azeotropic compositions as used herein include homogeneous azeotropes which are liquid admixtures of two or more substances that behave as a single substance, in that the vapor, produced by partial evaporation or distillation of the liquid, has the same composition as the liquid. Azeotropic compositions as used herein also include heterogeneous azeotropes where the liquid phase splits into two or more liquid phases. In these embodiments, at the azeotropic point, the vapor phase is in equilibrium with two liquid phases and all three phases have different compositions. If the two equilibrium liquid phases of a heterogeneous azeotrope are combined and the composition of the overall liquid phase calculated, this would be identical to the composition of the vapor phase.

For the purpose of this discussion, near-azeotropic composition means a composition that behaves like an azeotrope (i.e., has constant boiling characteristics or a tendency not to fractionate upon boiling or evaporation). Thus, the composition of the vapor formed during boiling or evaporation is the same as or substantially the same as the original liquid composition. Hence, during boiling or evaporation, the liquid composition, if it changes at all, changes only to a minimal or negligible extent. This is to be contrasted with non-azeotropic compositions in which during boiling or evaporation, the liquid composition changes to a substantial degree.

Near-azeotropic compositions exhibit dew point pressure and bubble point pressure with virtually no pressure differential. That is to say that the difference in the dew point pressure and bubble point pressure at a given temperature will be a small value, and in some near-azeotrope compositions the difference in dew point pressure and bubble point pressure of less than or equal to 3 percent (based upon the bubble point pressure).

It is also recognized that both the boiling point and the weight percentages of each component of the azeotropic or near-azeotropic liquid composition may change when the azeotropic or near-azeotropic liquid composition is subjected to boiling at different pressures. Thus, an azeotropic or a near-azeotropic composition may be defined in terms of the unique relationship that exists among the components or in terms of the compositional ranges of the components or in terms of exact weight percentages of each component of the composition characterized by a fixed boiling point at a specified pressure. It is also recognized in the art that various azeotropic compositions (including their boiling points at particular pressures) may be calculated (see, e.g., W. Schotte Ind. Eng. Chem. Process Des. Dev. (1980) 19, 432-439). Experimental identification of azeotropic compositions involving the same components may be used to confirm the accuracy of such calculations and/or to modify the calculations at the same or other temperatures and pressures.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Where applicants have defined an invention or a portion thereof with an open-ended terms such as "comprising", it should be readily understood that (unless otherwise stated) that the description includes the terms "consisting essentially of" and "consisting of".

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the disclosed invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

EXAMPLES

The concepts described herein will be further described in the following examples, which do not limit the scope of the invention described in the claims.

Example 1

Example 1 demonstrates the conversion of HCFC-231bb into HCFC-235cb.

Into a 1 L Hostelry C autoclave, 100 g of 1,1,1,2,3-pentachloro-2-fluoropropane (HCFC-231 bb)(0.426 mole) and 256 grams hydrogen fluoride (12.8 mole) is charged. The reactor is heated to 130° C. After one hour, the reactor is cooled, and the contents transferred to a second reactor having 10 g antimony pentafluoride. The temperature is raised to 120° C. while hydrogen fluoride is supplied at the rate of 10 g per hour over a period of 3 hours. The reaction is conducted at this state for 20 hours while keeping the reaction temperature at this level. The autoclave is cooled to −70° C., and HCl present is vented. The remaining volatile products are collected by vacuum-line transfer into closed cylinder which is cooled to −70° C. while heating the autoclave. These volatiles are scrubbed in 20% aqueous HCl precooled to −60° C. and maintained near that temperature. The 48.0 g of colorless oil collected after scrubbing and water washing is found to contain 78% $CF_3CF_2CH_2Cl$ (HCFC-235cb), 8% $CF_3CF_2CH_2F$ (HFC-236cb), 8% $CF_3CClFCH_2Cl$ (HCFC-234bb) and 4% $CF_2ClCClFCH_2Cl$ (HCFC-233bb).

Example 2

Example 2 demonstrates phase studies of mixtures of HF and HFC-236cb.

A phase study was performed for a composition consisting essentially of HFC-236cb and HF, wherein the composition was varied and the vapor pressures were measured at both 22.3° C. and 72.2° C. Based upon the data from the phase studies, azeotrope compositions at other temperature and pressures have been calculated.

Table 2 provides a compilation of experimental and calculated azeotrope compositions for HF and HFC-236cb at specified temperatures and pressures.

TABLE 2

| Temperature, ° C. | Pressure, psi | Mole % HF | Mole % HFC-236cb |
|---|---|---|---|
| −6.1 | 15 | 55.1 | 44.9 |
| 11.2 | 30 | 52.5 | 47.5 |
| 22.6 | 45 | 50.9 | 49.1 |
| 31.3 | 60 | 49.8 | 50.2 |
| 38.4 | 75 | 48.9 | 51.1 |
| 40.7 | 105 | 47.6 | 52.4 |
| 42.6 | 150 | 46.1 | 53.9 |
| 72.6 | 195 | 45.0 | 55.0 |
| 83.3 | 255 | 43.9 | 56.1 |
| 91.9 | 315 | 43.1 | 56.9 |
| 102.0 | 405 | 41.7 | 58.3 |
| 108.0 | 490 | 36.9 | 63.1 |

Example 3

Example 3 demonstrates dew point and bubble point vapor pressures for mixtures of HFC-236cb and HF.

The dew point and bubble point vapor pressures for compositions disclosed herein were calculated from measured and calculated thermodynamic properties. The near-azeotrope range is indicated by the minimum and maximum concentration of HFC-236cb (mole percent, mol %) for which the difference in dew point and bubble point pressures is less than or equal to 3% (based upon bubble point pressure). The results are summarized in Table 3.

TABLE 3

| Temperature, ° C. | Azeotrope composition, mol % HFC-236cb | Near azeotrope compositions, mol % HFC-236cb | |
|---|---|---|---|
| | | Minimum | Maximum |
| −20 | 42.6 | 38.0 | 54.4 |
| 60 | 53.6 | 47.6 | 68.2 |
| 12 | 61.6 | 54.4 | 75.8 |

Example 4

Example 4 demonstrates phase studies of mixtures of HF and HCFC-235cb.

A phase study was performed for a composition consisting essentially of HCFC-235cb and HF, wherein the composition was varied and the vapor pressures were measured at both 22.3° C. and 72.2° C. Based upon the data from the phase studies, azeotrope compositions at other temperature and pressures have been calculated.

Table 4 provides a compilation of experimental and calculated azeotrope compositions for HF and HCFC-235cb at specified temperatures and pressures.

TABLE 4

| Temperature, ° C. | Pressure, psi | Mole % HF | Mole % HCFC-235cb |
|---|---|---|---|
| 8.3 | 15 | 82.7 | 17.3 |
| 26.4 | 30 | 79.6 | 20.4 |
| 38.2 | 45 | 77.7 | 22.3 |
| 47.1 | 60 | 76.2 | 23.8 |
| 54.4 | 75 | 75.1 | 24.9 |
| 66.1 | 105 | 73.3 | 26.7 |
| 79.3 | 150 | 71.4 | 28.6 |
| 89.5 | 195 | 70.1 | 29.9 |
| 100.4 | 255 | 68.8 | 31.2 |
| 109.3 | 315 | 67.7 | 32.3 |

TABLE 4-continued

| Temperature, °C. | Pressure, psi | Mole % HF | Mole % HCFC-235cb |
|---|---|---|---|
| 120.0 | 405 | 66.2 | 33.8 |
| 127.1 | 480 | 65.1 | 34.9 |

Example 5

Example 5 demonstrates dew point and bubble point vapor pressures for mixtures of HCFC-235cb and HF.

The dew point and bubble point vapor pressures for compositions disclosed herein were calculated from measured and calculated thermodynamic properties. The near-azeotrope range is indicated by the minimum and maximum concentration of HCFC-235cb (mole percent, mol %) for which the difference in dew point and bubble point pressures is less than or equal to 3% (based upon bubble point pressure). The results are summarized in Table 5.

TABLE 5

| Temperature, °C. | Azeotrope composition, mol % HCFC-235cb | Near azeotrope compositions, mol % HCFC-235cb | |
|---|---|---|---|
| | | Minimum | Maximum |
| −20 | 12.1 | 11.4 | 12.9 |
| 60 | 25.8 | 23.4 | 29.1 |
| 120 | 33.8 | 30.0 | 38.9 |

Example 6

Example 6 demonstrates azeotropic distillation for separation of HFC-236cb from HFCF-235cb.

A mixture of HF, HFC-236cb and HCFC-235cb is fed to a distillation column for the purpose of purification of the HFC-236cb. The data in Table 6 were obtained by calculation using measured and calculated thermodynamic properties. The distillation column contains 30 theoretical stages with the feed located 10 stages from the bottom. The column operates at 24.7 psia (10 psig) with a molar reflux ratio of 3.0.

TABLE 6

| Compound or variable | Column feed | Column overhead (distillate) | Column bottoms |
|---|---|---|---|
| HCFC-235cb, | 27.3 mol % | 1 ppm (mole basis) | 99.99 mol % |
| HFC-236cb, | 63.6 mol % | 87.5 mol % | 130 ppm |
| HF, | 9.1 mol % | 12.5 mol % | trace |
| Temp, °C. | 0 | 7.2 | 43.4 |
| Pressure, psia (kPa) | 44.7 | 24.7 | 25.3 |

Example 7

Example 7 demonstrates separation of HFC-236cb and HF via two column pressure swing distillation.

A mixture of HF and HFC-236cb is fed to a distillation process for the purpose of purification of the HF-236cb. The data in Table 7 were obtained by calculation using measured and calculated thermodynamic properties. The numbers at the top of the columns refer to FIG. 2. Referring to FIG. 2, the first column, 700, contains 15 theoretical stages with the feed located 10 stages from the bottom. The column operates at 314.7 psia (300 psig) with a molar reflux ratio of 0.2. The second column, 800, contains 17 theoretical stages with the feed located 12 stages from the bottom. The column operates at 16.7 psia (2 psig) with a molar reflux ratio of 0.1.

TABLE 7

| Compound or variable | 510 Feed Mixture | 710 Column (700) distillate | 720 Column 700 Bottoms | 810 Column (800) distillate | 820 HFC-236cb product |
|---|---|---|---|---|---|
| HF, | 50 mol % | 44.10 mol % | 100.0 mol % | 52..76 mol % | 1 ppm (mole basis) |
| HFC-236cb, | 50 mol % | 55.9 mol % | 1 ppm (mole basis) | 47.24 mol % | 100 mol % |
| Temp., °C. | −5.0 | 91.8 | 132.6 | −3.5 | 2.4 |
| Pres., psia (kPa) | 64.7 | 314.7 (2169.6) | 314.8 (2170.4) | 16.7 (115.1) | 16.9 (116.5) |

Example 8

Example 8 demonstrates separation of HCFC-235cb and HF via two column pressure swing distillation.

A mixture of HF and HCFC-235cb is fed to a distillation process for the purpose of purification of the HCFC-235cb. The data in Table 8 were obtained by calculation using measured and calculated thermodynamic properties. The numbers at the top of the columns refer to FIG. 2. Referring to FIG. 2, a 50/50 molar mixture of HF and HCFC-235cb is fed to a first distillation column (700) containing 12 theoretical stages. Column 700 operates with a top pressure of 16.7 psia (2 psig) and a molar reflux ratio of 0.1. Purified HCFC-235cb is recovered as the bottom stream from this first column. The second distillation column (800) contains 15 theoretical stages with the feed added to the 4th stage from the top of the column. Column 800 operates with a top pressure of 314.7 psia (300 psig) and a molar reflux ratio of 0.1. Purified HF is removed as the bottoms product from column 800.

TABLE 8

| Compound or variable | 510 Feed Mixture | 710 Column (700) distillate | 720 Column 700 Bottoms | 810 Column (800) distillate | 820 HCFC-235cb product |
|---|---|---|---|---|---|
| HF | 50.0 mol % | 81.9 mol % | 1 ppm (mole basis) | 52.76 mol % | 1 ppm (mole basis) |
| HCFC-235cb | 50.0 mol % | 18.1 mol % | 100.0 mol % | 47.24 mol % | 100 mol % |
| Temp., °C. | 25.0 | 10.6 | 31.6 | −3.5 | 2.4 |
| Pres., psia (kPa) | 64.7 (446) | 16.7 (115) | 16.8 (116) | 314.7 (2170) | 314.8 (2170) |

Many aspects and embodiments have been described above and are merely exemplary and not limiting. After reading this specification, skilled artisans appreciate that other aspects and embodiments are possible without departing from the scope of the invention. Other features and benefits of any one or more of the embodiments will be apparent from the following detailed description, and from the claims.

And, not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. An azeotropic or near-azeotropic composition comprising from about 11.4 mole percent to about 38.8 mole percent 1,1,1,2,2-pentafluoro-3-chloropropane, and from about 61.2 mole percent to about 88.6 mole percent hydrogen fluoride.

2. The azeotropic composition of claim 1, comprising from about 17.3 mole percent to about 34.9 mole percent 1,1,1,2,2-pentafluoro-3-chloropropane and from about 65.1 to about 82.7 mole percent hydrogen fluoride.

3. The near-azeotropic composition of claim 2 comprising from about 11.4 mole percent to about 38.8 mole percent 1,1,1,2,2-pentafluoro-3-chloropropane and from 61.2 to 88.6 mole percent hydrogen fluoride, wherein the vapor pressure is from about 4.2 psia to about 245.6 at a temperature of from about −20° C. to about 120° C.

4. A process for the separation of 1,1,1,2,2-pentafluoro-3-chloropropane from a mixture comprising an azeotropic or near-azeotropic composition of 1,1,1,2,2-pentafluoro-3-chloropropane and hydrogen fluoride, said process comprising:
   a) subjecting said mixture to a first distillation step in which a composition enriched in either (i) hydrogen fluoride or (ii) 1,1,1,2,2-pentafluoro-3-chloropropane is removed as a first distillate composition with a first bottoms composition being enriched in the other of said components (i) or (ii); and
   b) subjecting said first distillate composition to a second distillation step conducted at a different pressure than the first distillation step in which the component enriched as first bottoms composition in (a) is removed as an azetotrope in a second distillate composition with a second bottoms composition enriched in the same component which was enriched in the first distillate composition.

5. The process of claim 4 wherein said second distillation step is carried out at a pressure greater than the pressure of the first distillation step.

6. The azeotropic composition of claim 2, having a vapor pressure of from about 15 psia to about 480 psia, at a temperature of from about 8.2 ° C. to about 127.1° C.

7. An azeotropic or near-azeotropic composition consisting essentially of from about 11.4 mole percent to about 38.8 mole percent 1,1,1,2,2-pentafluoro-3-chloropropane, and from about 61.2 mole percent to about 88.6 mole percent hydrogen fluoride.

8. The azeotropic composition of claim 7, consisting essentially of from about 17.3 mole percent to about 34.9 mole percent 1,1,1,2,2-pentafluoro-3-chloropropane and from about 65.1 to about 82.7 mole percent hydrogen fluoride.

9. The near-azeotropic composition of claim 7 consisting essentially of from about 11.4 mole percent to about 38.8 mole percent 1,1,1,2,2-pentafluoro-3-chloropropane and from 61.2 to 88.6 mole percent hydrogen fluoride, wherein the vapor pressure is from about 4.2 psia to about 245.6 at a temperature of from about −20° C. to about 120° C.

10. The azeotropic composition of claim 7, having a vapor pressure of from about 15 psia to about 480 psia, at a temperature of from about 8.2° C. to about 127.1° C.

* * * * *